United States Patent [19]
Bruno

[11] Patent Number: 5,776,239
[45] Date of Patent: Jul. 7, 1998

[54] HYDROTHERMAL PROCESS FOR MAKING ULTAFINE METAL OXIDE POWDERS

[75] Inventor: Salvatore Anthony Bruno, Wilmington, Del.

[73] Assignee: E. I. Du Pont de Nemours and Company, Wilmington, Del.

[21] Appl. No.: 918,702

[22] Filed: Aug. 22, 1997

Related U.S. Application Data

[63] Continuation of Ser. No. 548,987, Oct. 27, 1995, abandoned.

[51] Int. Cl.$^6$ ............................................. C09C 1/36
[52] U.S. Cl. .................... 106/437; 106/425; 106/426; 106/428; 106/430; 106/431; 106/436; 106/453; 106/455; 423/610; 423/611; 423/612; 423/616
[58] Field of Search ........................... 423/610, 611, 423/612, 616; 106/436, 437, 425, 426, 428, 430, 431, 453, 455

[56] References Cited

U.S. PATENT DOCUMENTS

| | | | |
|---|---|---|---|
| 2,113,946 | 4/1938 | Plechner et al. | 423/612 |
| 2,232,817 | 2/1941 | Verduin | 423/612 |
| 2,290,922 | 7/1942 | Verduin | 423/612 |
| 3,105,743 | 10/1963 | Cobb | 423/612 |
| 3,862,297 | 1/1975 | Calridge et al. | 423/616 |
| 4,018,876 | 4/1977 | Jordan | 423/421 |
| 4,803,291 | 2/1989 | Rousset et al. | 252/62.55 |
| 4,814,318 | 3/1989 | Hums | 502/439 |
| 4,954,476 | 9/1990 | Hums | 502/350 |
| 5,030,439 | 7/1991 | Brownbridge | 423/610 |
| 5,049,371 | 9/1991 | Rinn et al. | 423/612 |
| 5,068,056 | 11/1991 | Robb | 106/436 |
| 5,139,980 | 8/1992 | Nakahara et al. | 423/610 |
| 5,149,519 | 9/1992 | Chopin et al. | 423/612 |
| 5,180,585 | 1/1993 | Jacobson et al. | 424/405 |
| 5,196,388 | 3/1993 | Shyu | 501/134 |
| 5,215,580 | 6/1993 | Elfenthal et al. | 106/441 |
| 5,242,557 | 9/1993 | Jones et al. | 204/157 |
| 5,468,471 | 11/1995 | Zecchino et al. | 424/59 |
| 5,536,448 | 7/1996 | Takahashi et al. | 423/610 |
| 5,556,641 | 9/1996 | Lambridis et al. | 106/437 |

FOREIGN PATENT DOCUMENTS

| | | | |
|---|---|---|---|
| 2100224 | 7/1993 | Canada | C09C 1/36 |
| 444 798 | 9/1991 | European Pat. Off. | C01G 23/047 |
| 57-209824 | 3/1983 | Japan . | |
| 63-095119 | 4/1988 | Japan . | |
| 02 172805 | 9/1990 | Japan . | |
| 2-62498 | 12/1990 | Japan | C01G 25/04 |
| 4-166235 | 6/1992 | Japan | B01J 35/06 |
| 1795958 | 2/1993 | U.S.S.R. | C01G 23/053 |
| 2 221 901 | 8/1989 | United Kingdom | C01G 23/047 |
| WOA94 25397 | 11/1994 | WIPO . | |

OTHER PUBLICATIONS

Wang Xiaohui, Wang Zichen, LI Xi, Zhang Lihua and Xiao Liangzhi, Preparation of TiO2 Ultrafine Particles Using Collodial Method, *Department of Chemistry, Jilin University, Changchum 130023,* 6 No. 6:533–7, 1–12,1992–translation, (no month).

Humin Cheng, Jiming Ma, Zhenguo Zhao, and Limin Qi, Hydrothermal Preparation of Uniform Nanosize Rutile and Anatase Particles, *Chem. Mater.,* 7, 663–671, 1995, (no month).

*Primary Examiner*—Mark L. Bell
*Assistant Examiner*—Scott L. Hertzog

[57] ABSTRACT

An ultrafine titanium dioxide powder is disclosed that can be produced by hydrothermal treating an amino titanium oxalate composition. Ultrafine titanium dioxide powders are useful in cosmetic and other applications for controlling exposure to ultraviolet (UV) light.

5 Claims, 11 Drawing Sheets

HYDROTHERMAL PROCESS FOR MAKING ULTAFINE METAL OXIDE POWDERS

This a continuation of application Ser. No. 08/548,987 filed Oct. 27, 1995, now abandoned.

BACKGROUND OF THE INVENTION

U.S. Pat. No. 4,814,318 describes a titanium dioxide catalyst carrier formed by a hydrothermal process from a mixture of meta- and ortho-titanic acid with additives of rare earths, not including cerium, and one or more of the following: phosphate, sulfate and borate.

U.S. Pat. No. 4,954,476 describes a method to prepare a catalyst containing titanium dioxide as a primary ingredient in a hydrothermal process with meta- or ortho-titanic acid as starting material.

U.S. Pat. No. 5,030,439 describes a method to prepare particulate anatase titanium dioxide by reacting titanium tetrahalide with sulfuric acid at 65–100 degrees C. to first form titanyl sulfate which is subsequently crystallized then redissolved in water and hydrolyzed at 85–100 degrees C. to form $TiO_2$.

U.S. Pat. No. 5,242,557 describes a process to prepare pigmentary titanium dioxide by hydrothermal precipitation during which the reaction mixture is subjected to ultrasonic vibrations.

European Patent No. 0 444 798 describes a process to prepare microcrystalline particles of titanium dioxide with crystallite size <100 nm that involves (1) treating solid $TiO_2$, preferably a washed $TiO_2$ hydrate precipitate obtained from a sulfate process, with a base, preferably NaOH; (2) treating the precipitate from (1) with hydrochloric acid and (3) neutralizing the composition from (2) with NaOH or $Na_2CO_3$ and (4) after filtration and washing, optionally further treatment may be performed.

British Patent No. 2,221,901 describes a titanium dioxide pigment and a process for preparing the pigment by precipitation from titanium tetrachloride or titanium hydroxide mass from the conventional sulfate process in an aqueous medium with ammonia (as $NH_4OH$), sodium acetate, sodium oxalate or by diluting with water.

Japanese Unexamined (Kokai) Patent Application Publication No. 62-207718 describes a crystalline anatase titanium dioxide sol and a method for the manufacture of such sol. The process to prepare the anatase sol involves reacting a water soluble titanium compound (such as titanium tetrachloride, titanium sulfate) with an ammonium compound (such as aqueous ammonia, ammonium carbonate) to produce a gel and subsequent hydrothermal treatment of the gel.

Japanese Unexamined (Kokai) Patent Application Publication No. 4-166235 describes a lamelliform catalyst for removal of nitrogen oxides and the process to prepare such catalyst. The catalyst is typically tungsten supported on a calcium containing inorganic fiber fabric or mesh. The mesh is coated with a slurry containing a tungsten compound, fine particulate titanium oxide and/or oxides of zirconium or cordierite and at least one organic binder such as polyvinyl alcohol. Ammonium titanyl oxalate can be used as a reagent in the slurry to improve adhesion of the fine particulate $TiO_2$ to the mesh surface.

The disclosure of the aforementioned references is hereby incorporated by reference.

FIELD OF THE INVENTION

The present invention relates to a titanium dioxide powder and methods for making such powder.

SUMMARY OF THE INVENTION

The present invention provides an amino titanium oxalate composition and a process to prepare such a composition. The amino titanium oxalate can be prepared in the presence of at least one doping metal, which can be for example, tin, aluminum, antimony, zirconium, zinc, cerium, germanium, manganese, vanadium, ruthenium, iridium, osmium, tungsten, molybdenum, niobium, cobalt, lead, silicon, indium, tantalum, yttrium, iron, copper, nickel, among others. The amino titanium oxalate is useful as a precursor in a hydrothermal process to produce ultrafine titanium dioxide powders.

By "amino titanium oxalate" it is meant to refer to a substantially white crystalline solid that can be hydrolytically and/or thermally converted or decomposed. The structure of the amino titanium oxalate corresponds substantially to that shown in FIG. 3. Without wishing to be bound by any theory or explanation it is believed that the structure of the inventive amino oxalate is:

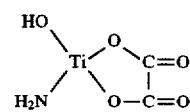

The ultrafine titanium dioxide powders of the invention are essentially transparent having an average crystallite size of about 1–100 nm, and usually from about 4–60 nm. By "essentially transparent" it is meant that when properly incorporated into an emulsion or a paint dispersion, applied to a substrate and allowed to dry, no residual whiteness can be visually detected.

The processes of the present invention can also be adapted to produce ultrafine particles of other inorganic metal oxides such as those of zinc, electrically conductive tin, e.g., antimony containing tin oxide, iron, zirconium, aluminum, chromium, yttrium, europium, mixtures thereof, among others.

The processes of the present invention can also be employed for coating inorganic metal oxides upon a wide range of core particles. Examples of such core particles include at least one member from the group of $TiO_2$, $ZrO_2$, $SiO_2$, $Al_2O_3$, $Y_2O_3$, $SnO_2$, $Sb_2O_3$, $Fe_2O_3$, AnO, $BaSO_4$, $CaSO_4$, $BaSiO_3$, $Ba(PO_4)_2$, $Ca(PO_4)_2$, $CaSiO_3$, $CaF_2$, $Zn_3(PO_4)_2$, $ZnSiO_3$, $ZnSiO_4$, $MgSiO_3$, $MgSiO_3$, $Mg(PO_4)_2$, among others. These core particles can include a plurality of coatings in addition to the inorganic metal oxide coating. Alternatively, the ultrafine metal oxide produced in accordance with the instant invention can be coated with one or more coatings. For example, the metal oxide of the instant invention can be used as a core particle and coated in the manner described in U.S. Pat. No. 5,180,585 and copending and commonly assigned U.S. Pat. application No. 08/139,962 (corresponding to PCT Patent Application Publication No. WO95/10940); both of which are hereby incorporated by reference, thereby producing an antimicrobial powder. Further, the ultrafine metal oxide of the invention could be coated with one or more layers which are associated with an electrically conductive tin oxide, e.g., ultrafine titania coated with a silica-containing layer that is in turn coated with electrically conductive tin oxide. One suitable method for applying an electrically conductive tin oxide upon a core particle is disclosed by U.S. patent application Ser. No. 07/386,765 (corresponding to European Patent Application Publication No. 0 359 569); the disclosure of which is hereby incorporated by reference.

While hydrothermal processes are known, the present invention uses a novel amino titanium oxalate as a precursor or reagent in a novel hydrothermal process to produce ultrafine $TiO_2$ powders. The advantages to using an amino titanium oxalate for producing ultrafine $TiO_2$ powders include: (1) rutile, the high temperature phase of $TiO_2$, is produced exclusively at relatively low temperatures, (2) a desirable particle size can be achieved, (3) uniform sized ultrafine particles, among other advantages.

In contrast to the instant invention, conventional processes for making titania are non-selective, i.e., both rutile and anatase are formed. Further, conventional hydrothermal processes employ additional calcination steps, particularly if rutile is desired, which are time consuming and expensive. The present invention requires no calcination step. Calcination also generally leads to coarse agglomerates which cause reduced transparency.

The ultrafine titania of the invention can be a component of an improved sunscreen. Examples of conventional sunscreens are described in "Formulating With A Physical Sun Block", Dahms, Cosmetics & Toiletries, Vol. 107, October 1992, Pages 133 to 143; the disclosure of which is hereby incorporated by reference. Conventional sunscreens are typically based on organic ultraviolet (UV) light absorbers which may have associated with them one or more of the following problems: (1) expensive; (2) limited to protection only from UV A or B radiation. A combination of several organic UV-Absorbers is generally required to provide both a high SPF (sun protection factor) and a high MAR (mean absorbance ratio). UV-A radiation is believed to contribute to skin aging, dermatological photosensitivity, among other skin ailments. It is believed that in some cases use of high UV-B protection sun products may exacerbate the potential for UV-A induced skin ailments or damage by increasing exposure to UV-A radiation.

Rutile titanium dioxide is opaque to UV light and, therefore, can be a useful ingredient in sunscreen formulations. Currently, limited commercial acceptance of conventional $TiO_2$ in sunscreens may be attributed to an undesirable whiteness, e.g., associated with $TiO_2$ when applied to the skin. In comparison to conventional $TiO_2$, the ultrafine $TiO_2$ particles of the invention are essentially transparent to visible light; but are opaque to UV light. The use of the inventive ultrafine $TiO_2$ in sunscreens may have the following advantages over conventional organic absorbers: (1) less expensive; (2) provides protection from both UV-A and UV-B radiation; (3) substantially biologically and chemically inert; (4) acceptable in cosmetics; (5) low potential for causing irritancy to the body, among other advantages.

Ultrafine titanium dioxide of the invention can also be useful in other applications wherein it is desirable to absorb ultraviolet light such as in cosmetics or personnel care products, within or upon packaging material for food or other materials such as wood coatings, coatings on vinyl and other architectural materials, glass, automotive clearcoats, automotive basecoats (for the so-called "flip-flop" effect) that may be subject to degradation by UV light, among many other applications.

Ultrafine titania and metal oxide powders of this invention, which optionally are doped with a second metal, can be employed in a wide range of industrial applications such as in paints, catalysts and catalyst supports (especially for use in the treatment of waste streams), temperature sensors, ceramic coated films, electroconductive powders, cutting tools, among other engineered materials applications for ceramic powders.

CROSS-REFERENCE TO RELATED PATENT OR PATENT APPLICATION

The subject matter of this invention is related to copending and commonly assigned U.S. patent application Ser. No. 08/548,988 (Attorney's Docket No. CH-2546) filed on even date herewith in the name of Donald D. May, entitled "Dispersants for Inorganic Materials In Aqueous Systems"; the disclosure of which is hereby incorporated by reference.

BRIEF DESCRIPTION OF THE DRAWINGS

In FIGS. 1, 3, 4, 6, 8 and 10, the x-axis corresponds to degrees 2-theta and the y-axis corresponds to intensity in counts per second. Pertinent reference patterns, e.g., rutile and brookite, are presented below the X-ray diffraction patterns for comparison.

DETAILED DESCRIPTION

Figure 1:
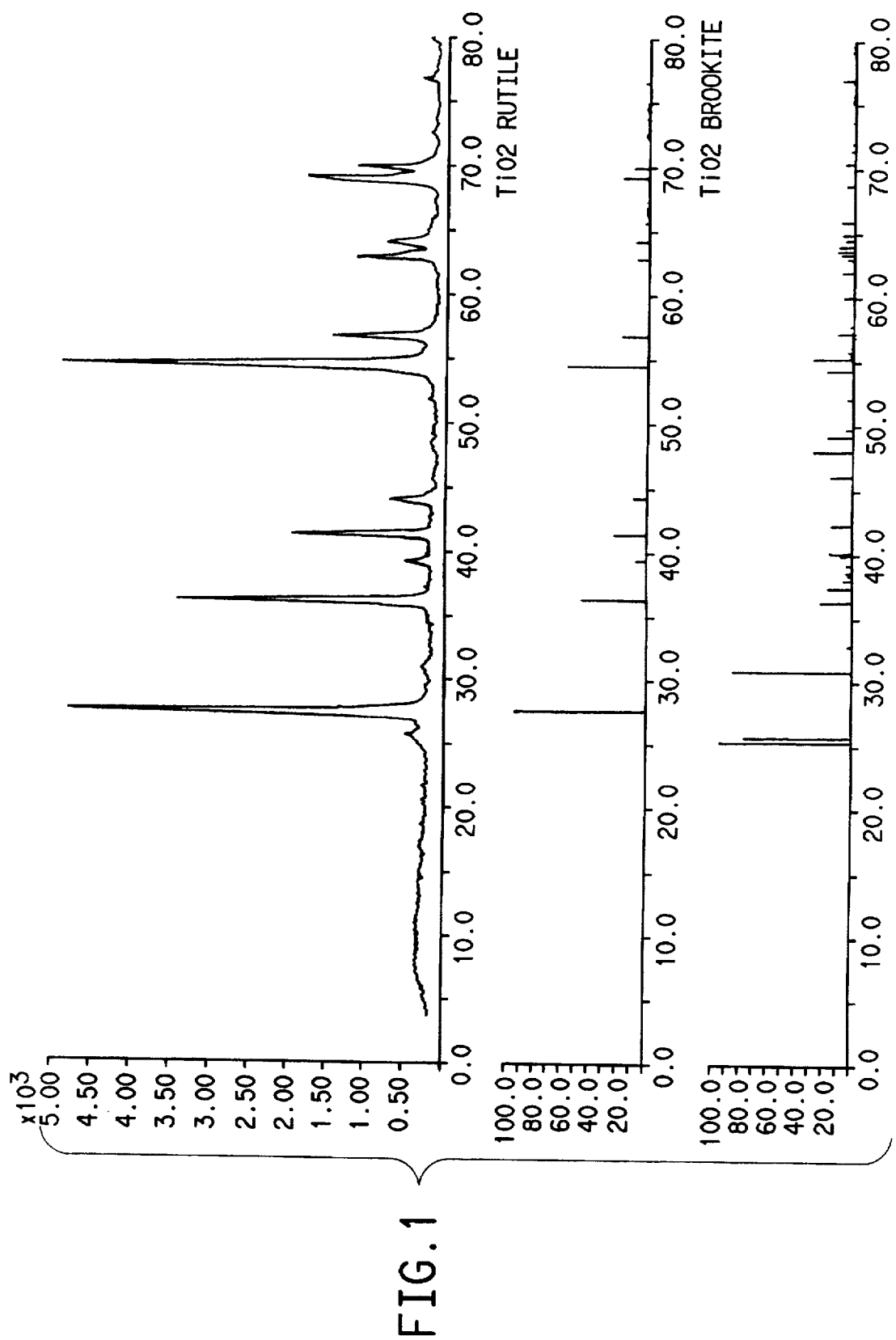
FIG. 1 is an X-ray diffraction pattern for the powder produced in accordance with Example 1B.

The present invention provides a novel amino titanium oxalate that can be produced by contacting a hydrolyzable titanium compound with oxalic acid followed by contact with aqueous ammonia.

In one aspect of the invention, the amino titanium oxalate can optionally be prepared while in the presence of at least one dopant metal such as Sn, Al, among others, which can decrease crystallite size and provide more uniform particle size. The X-ray diffraction pattern of the amino titanium oxalate of this invention differs from the X-ray diffraction pattern of ammonium titanyl oxalate, $TiO(C_2O_4)_2(NH_4)_2$.

The amino titanium oxalate can be converted by using a hydrothermal process into ultrafine titanium dioxide powders. The ultrafine titanium dioxide powders of the present invention are substantially in the rutile phase as determined by X-ray diffraction patterns, e.g., the powder comprises about 95 to about 100 wt % rutile. The powders have a primary crystallite size of from about 1 to 100 nm, usually from about 4 to about 60 nm. These crystallites can form agglomerates with an average size up to about 300 nm. The specific surface area of the powders is typically about 20 to about 150 m2/g, normally from about 30–90 m2/g. Transmission electron micrographs (TEM's) have shown that the $TiO_2$ can be in the form of acicular platelets with an aspect ratio of about 4 to 1.

The ultrafine titanium dioxide powders can be used in cosmetic or personnel care product applications. These powders can provide improved spreading and a smoother touch while providing excellent ultraviolet (UV A/B) screening properties and being essentially transparent to visible light. The properties of the ultrafine titanium dioxide powders of the present invention also render these powders ideal for use in sunscreens, packaging materials such as for food to reduce UV degradation, clear coatings and varnishes to provide barriers to UV radiation, among other uses. The $TiO_2$ powders can also act as catalysts or catalyst supports, or due to its ability to absorb ultraviolet radiation these powders can act as photocatalysts. Such photocatalyst can be used for treating waste streams e.g., in environmental clean-up to accelerate photodegradation of an oil spill.

The aforementioned amino titanium oxalate can be prepared by a process comprising the following steps: (1) an aqueous solution comprising oxalic acid is prepared, (1') optionally an aqueous, organic or aqueous-organic solution comprising at least one hydrolyzable titanium compound is prepared, e.g., at least one member from the group of titanyl sulfate, titanium oxychloride, titanium tetrachloride, titanium alkoxides, TYZOR-TE™ (a triethanolamine chelate of titanium supplied by E. I. du Pont de Nemours and Company, Wilmington, Del.) TYZOR-LA™ (a lactic acid ammonium salt chelate of titanium supplied by E. I. du Pont de Nemours and Company, Wilmington, Del.), among others, (2) a hydrolyzable titanium compound or a solution of the titanium compound is added to the aqueous solution of oxalic acid, (2') optionally, additional deionized water is added to the solution containing the titanium complex and oxalic acid, (3) a concentrated ammonium hydroxide solution is added to the solution containing the titanium compound and oxalic acid, (4) the pH of the solution is adjusted to about 8–10 and the resulting slurry containing a white solid is stirred for approximately 30 minutes, and; (5) the white amino titanium oxalate product is recovered by filtration from the aqueous slurry, washed, and dried.

In one aspect of the invention, the amino titanium oxalate can be prepared by a process that comprises contacting a hydrolyzable titanium compound with oxalic acid followed by contact with aqueous ammonia. A concentrated aqueous solution comprising oxalic acid can be prepared by charging deionized water and oxalic acid dihydrate into a pressure vessel or flask that is normally maintained under an atmosphere of nitrogen. This solution can be warmed from ambient temperature to from about 40 to 60 degrees C. to aid in dissolution of the oxalic acid.

An aqueous solution comprising a water soluble titanium precursor or reagent such as titanium oxychloride can be added to the oxalic acid solution. The water soluble titanium complex can be added over a temperature range of from about 0–70 degrees C. For such reagents, the oxalic acid solution can be heated to a temperature of from about 40 to 60 degrees C. Alternatively, if the titanium reagent is a susceptible to very rapid hydrolysis, it may be added neat to the oxalic acid solution. Examples of such titanium reagents include titanium tetrachloride, titanium alkoxides such as TYZOR-TPT™ (tetraisopropyl titanate supplied by E. I. du Pont de Nemours and Company, Wilmington, Del.), TYZOR-TBT™ (tetrabutyl titanate supplied by E. I. du Pont de Nemours and Company, Wilmington, Del.), among others. For these reagents, it can be desirable to cool the oxalic acid mixture to a temperature of from about 5 to about 10 degrees C.

The amount of titanium reagent in liquid form or dissolved in an aqueous solution provides approximately an 1:1 molar ratio with the oxalic acid reagent. While a mole ratio of titanium to oxalic acid of about 1:1 is desired, the range can be from about 0.9:1 to 1.1:1.

The aqueous solution of the titanium complex or liquid titanium complex can be added to the reaction vessel or flask containing the oxalic acid solution while stirring. Normally, the addition occurs under an atmosphere of nitrogen.

Following addition of the titanium reagent, the resulting mixture can be stirred while optionally being heated to a temperature of about 30 degrees C. to provide a clear solution. Concentrated aqueous ammonium hydroxide solution (about 29.5% $NH_3$) can be added to the clear titanium/oxalic acid solution in a dropwise manner with stirring of the solution over a period of time from about 40 minutes to 2 hours. The ammonium hydroxide can be added at a rate to maintain a temperature of about 25 to 30 degrees C. A white slurry is produced with a pH of about 9. The slurry can be stirred for about 30 minutes after adding the concentrated ammonium hydroxide solution, while the pH is being maintained at about 8–10 by the addition of small amounts of ammonium hydroxide.

After addition of the ammonium hydroxide is complete, a white product comprising an amino titanium oxalate is recovered by standard techniques, for example, by filtration methods, from the aqueous slurry. The white solid can be washed with several volumes of a 2% ammonium hydroxide solution. The solid can be dried in an oven at a temperature greater than 100 degrees C., normally 100–120 degrees C.

In another aspect of the invention, it has been found useful to add certain dopant metals to the hydrolyzable titanium compound and/or the oxalic acid solution. The presence of these dopant metals, e.g. tin and aluminum, can cause a reduction in the particle size of ultrafine metal oxides, e.g., ultrafine titania, which are obtained from the doped oxalate. These dopant metals can be present in the final ultrafine metal oxide powders at concentrations of about 0 to at 10 least 20% based on weight of the metal oxide.

In yet another aspect of the invention, dopant metals can be an oxide of one or more of the following: tin, aluminum, antimony, zirconium, zinc, cerium, germanium, manganese, vanadium, ruthenium, iridium, osmium, tungsten, molybdenum, niobium, cobalt, lead, silicon, indium, tantalum, yttrium, iron, arsenic, nickel, among others. The aforementioned dopant metals can be added to the hydrolyzable titanium compound and/or the oxalic acid solution. These dopant metals can be present in the final ultrafine metal oxide powders at concentrations of about 0 to at least 20% based on weight of the metal oxide.

The dopant metals can be added as hydrolyzable metal complexes or salts. The source of the dopant metal can be introduced in any suitable manner such as being added to the hydrolyzable compound titanium either in the same solution with the titanium compound or separate from the titanium. The dopant metal can also be added to the oxalic acid solution immediately before or after addition of the titanium compound. Normally, the dopants are added before adding the concentrated base which precipitates the oxalate.

A procedure to prepare the ultrafine titanium dioxide powders in this invention comprises hydrothermal treatment of any suitable amino titanium oxalate, e.g., prepared by reacting a hydrolyzable titanium compound with oxalic acid followed by reaction with aqueous ammonium hydroxide solution. Hydrothermal treatment of the present invention can comprise a reaction with water at an elevated temperature in a closed vessel under pressure. The amino titanium oxalate product of the present invention can be used to prepare ultrafine titanium dioxide powder by the following steps: (1) charging amino titanium oxalate and deionized water into an autoclave, shaker tube or other pressure vessel capable of withstanding pressure up to about 3000 psi, (2) sealing the pressure vessel and the heating contents to a temperature of about 200–250 degrees C. with agitation for about 2–5 hours, (3) cooling the pressure vessel, recovering the ultrafine titanium dioxide product washing and drying the recovered product.

For example, an amino titanium oxalate and deionized water, normally up to about 1.1 lb. of $TiO_2$ per gallon, can be charged to a pressure vessel constructed of corrosion resistant materials e.g., tantalum, zirconium or titanium, such as a shaker tube or autoclave. The pressure vessel is sealed and heated to a temperature of about 180–250 degrees C., preferably 200–205 degrees C. while the mixture within the pressure vessel is agitated.

After heating for about 2–5 hours, the pressure vessel is cooled to about 25–50 degrees C. A white titanium dioxide product is recovered from the slurry product, for example, by filtration, and washed with several volumes of deionized water until the filter cake is substantially free from salts as determined by conductance measurements. The wet product is dried in an oven, preferably a vacuum oven at a temperature in excess of 100 degrees C. which then provides ultrafine titanium dioxide powder.

The ultrafine powders of the instant invention can absorb ultraviolet radiation and, therefore, are useful within cosmetics, sunscreens, among other personnel care products. One measure of ultraviolet radiation absorbance is by determining the SPF and MAR for these powders. Determinations of sun protection factors (SPF) and mean absorbance ratios (MAR) of ultrafine powders prepared by the processes of the present invention were performed in the manner described by Diffey and Robson in J. Soc. Cosmet. Chem. 1989, 40, pp. 127–133; hereby incorporated by reference. An Optometrics SPF-290 Analyzer (available from Optometrics U.S.A., Inc., Ayer, Mass.), described by Sellers and Carpenter in Cosmetics & Toiletries 1992, 107, pp. 119–122; hereby incorporated by reference, was used. For the present invention, however, a polypropylene sheet was used as the substrate to coat with the dispersions of ultrafine powders instead of the surgical tape used in the above references.

The calculations involved for determining SPF are described in the incorporated Diffey and Robson reference. SPF is based on a calculation which involves a sum from 290 to 400 nm of the ratio of E(1), the spectral irradiance of terrestrial sunlight under defined conditions multiplied by B(1), and the relative effectiveness of UV radiation at a specified wavelength in producing delayed erythema (redness) in human skin. This calculation is described in greater detail in CIE Journal 1987, 6, pp. 17–22; the disclosure of which is hereby incorporated by reference.

Mean (average) absorbance ratio or MAR is the UV-A/UV-B ratio or the total absorbance, (integrated area in the UV-A region (320–400 nm)), divided by the total absorbance, (integrated area in the UV-B region (290–320 nm)). The MAR of sun protection agents will typically vary from 0 to 1, with 0 indicating no UV-A absorbance and 1 indicating UV-A absorbance equal to UV-B absorbance.

The ultrafine powders of the invention also possess a desirable transparency when incorporated within a suitable matrix, e.g., a coating, fiber or film. Transparency of the ultrafine powders is determined by haze measurements of films containing the powders on transparent substrates. Haze is a measure of the percent of light that is scattered as the light passes through a sample mounted in a Hunter ColorQuest instrument determined by transmittance measurements. The maximum value for transparency is 93% for the sheets used in the below examples. The lower the haze value, the less light is scattered, the more transparent is the sample.

While the above description has focused on the preparation of ultrafine titanium dioxide powders, the process of the present invention can also be used to prepare other ultrafine metal oxide powders, for example, ultrafine metal oxide powders of zinc, iron, zirconium, aluminum, chromium, yttrium, tin oxide, and europium among others. Ultrafine powders of zinc oxide, aluminum oxide, tin oxide, optionally along with a dopant metal can also be prepared substantially in accordance with the following procedures. These ultrafine metal oxides can be also coated as desired, or applied as a coating upon a virtually unlimited array of materials.

The following Examples illustrate certain aspects of the present invention, and do not limit the scope of the invention defined in the appended claims.

The X-ray diffraction patterns described in the following Examples were generated on a Philips APD 1710 diffractometer in accordance with conventional procedures. The TEMs discussed in the following Examples were obtained by using a Philips CM12 microscope operating at 120 kilovolts and in accordance with conventional procedures. TEM samples were prepared by dispersing a sample in ethyl alcohol and piptetting the dispersion onto the TEM sample grid.

A dispersion that is described in the following Examples comprises a resin and metal oxide. The dispersion is uniformly spread onto a transparent support using a Bird applicator or wire wound rod, according to standard industrial techniques, e.g., Mylar™ film, this is called a drawdown. A Hunter ColorQUEST, D65 illuminant, 2 degrees observer angle machine is used to provide and collect the light from the coated support. The light is shone through a 1" diameter section of the coated support. Both the amount of transmitted diffuse light and total transmitted light may be measured. The % Haze=100x (diffuse transmitted/total transmitted). Coated samples of less than 10% Haze are characterized as marginally transparent whereas those with a Haze of less than 3% are characterized as transparent. A lower % Haze corresponds to a higher transparency.

The characteristics of a drawdown can also be measured by using spectrophotometric techniques. An Optometrics SPF290 UV spectrophotometer can be employed to analyze emulsion samples. An emulsion containing the inventive metal oxide is spread upon a TRANSPORE™ tape (3M Company, St. Paul, Minn.) and analyzed on the SPF290 to determine SPF & MAR. If the monochromatic protection factor (MPF) at 400 nm is less than 2 units, then the emulsion or drawndown is characterized as being transparent. On conventional UV/visible spectrophotometers, a reading of less than 0.2 absorbance units at 500 nm is characterized as being transparent.

EXAMPLE 1

(A) Preparing amino titanium oxalate from titanium oxychloride:

Approximately 500g of deionized water and oxalic acid dihydrate, about 126.1 g (1.0 mole) were charged into a 2-liter flask that was maintained under a nitrogen atmosphere. The resultant slurry was warmed to a temperature of about 40 degrees C. to dissolve the oxalic acid.

A titanium oxychloride solution (about 383.2 g, 12.5% by weight titanium 1.0 mole), was prepared and was added rapidly to the oxalic acid slurry with stirring at a temperature of from about 40 to about 60 degrees C. The resulting clear solution was cooled to about 25 degrees C. Concentrated ammonium hydroxide solution was added dropwise over a period of about 40 minutes at a temperature of from 25 to 30 degrees C. to provide a white slurry with a pH of about 9. The slurry was stirred for 30 minutes while the pH was maintained at about 9.0 by the addition of small increments of ammonium hydroxide. The total amount of concentrated ammonium hydroxide (29.5% $NH_3$) consumed was about 410.9 g (7.12 moles). The white slurry was filtered and the filter cake washed with six 400 ml displacement washes of 2% ammonium hydroxide. The wet cake was dried at about 120 degrees C. in a vacuum oven to provide approximately 156.5 g of amino titanium oxalate.

(B) Preparing ultrafine titanium dioxide by the hydrothermal decomposition of amino titanium oxalate:

Approximately 40 g of amino titanium oxalate from produced in accordance with Example 1, part (A), and about 250 g of deionized water were charged to a 400 ml tantalum shaker tube. The shaker tube was sealed and the contents heated at a temperature of about 200 to 205 degrees C. for about 3 hours while gently shaking. The shaker tube was cooled to about 25 degrees C. and the resulting white slurry filtered. The filter cake was washed with about 2600 ml of deionized water. The wet cake, which weighed about 34.4 g, was dried in a vacuum oven at about 120 degrees C. to provide about 20.1 g of ultrafine titanium dioxide.

Referring now to FIG. 1, FIG. 1 is an X-ray diffraction pattern of the dried ultrafine titanium dioxide. The X-ray diffraction indicates that the dried titanium dioxide powder to be mostly rutile with a trace of brookite. The rutile primary crystallite size as determined by X-ray line broadening was about 41 nm. The average agglomerate size (D50) determined by using a Microtrac Particle Analyzer (available from Leeds & Northrup Corporation, St. Petersburg, Fla.) to be about 0.17 microns. The specific surface area of this ultrafine titanium dioxide was about 54.9 m2/g.

Figure 2:
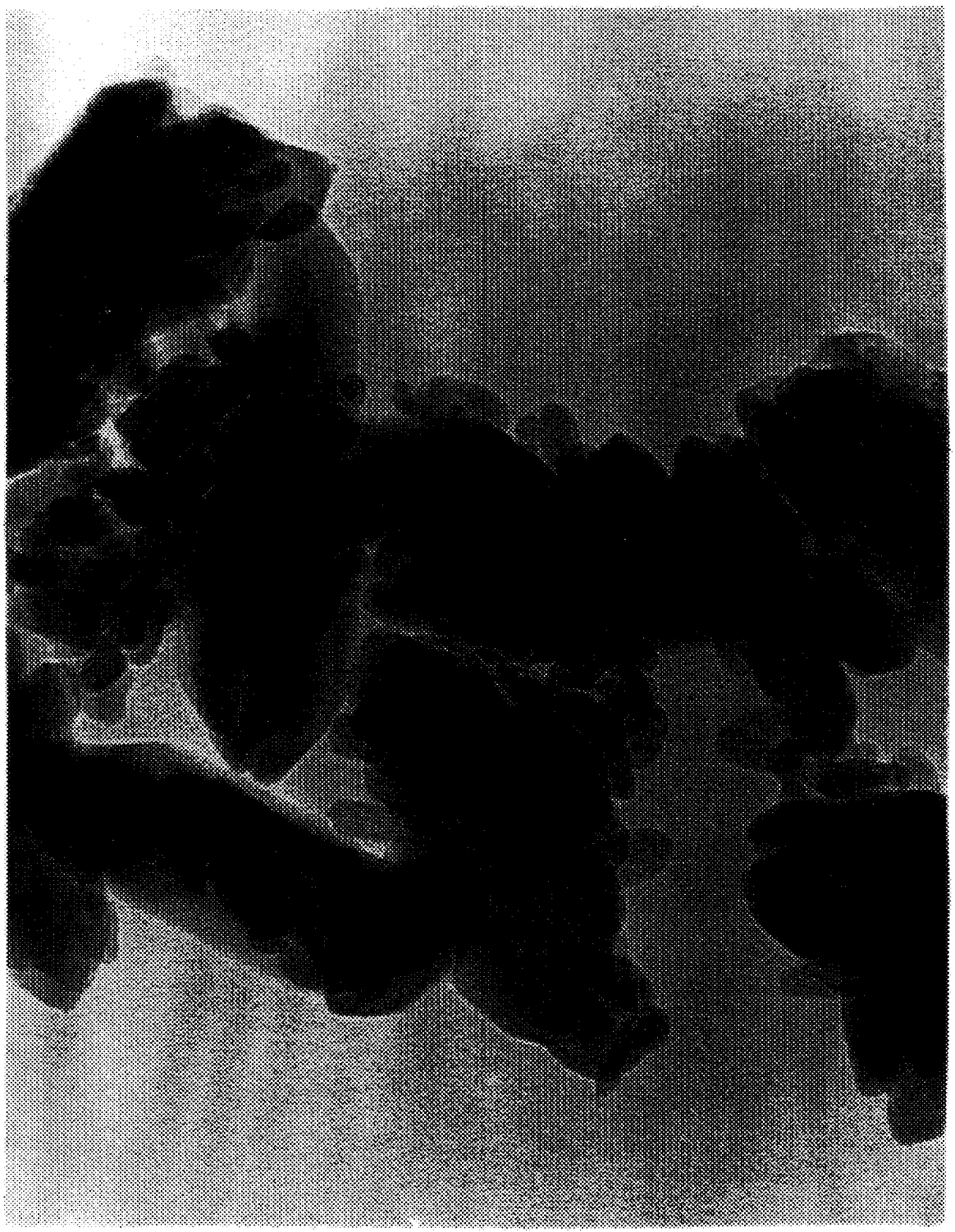
FIG. 2 is a transmission electron micrograph (TEM) for the powder produced in accordance with Example 1B.

Referring now to FIG. 2, FIG. 2 is a TEM taken at 3×160 Kx magnification wherein 1 cm=21 nm.

EXAMPLE 2

(A) Preparing amino titanium oxalate from titanium tetrachloride:

Approximately 1,000 g of deionized water and oxalic acid dihydrate (381.9 g, 99% 3.0 moles), were charged to a 5-liter flask that was maintained under a nitrogen atmosphere. The resultant slurry was cooled to about 5 to 10 degrees C. and approximately 569.1 g (3.0 moles) of titanium tetrachloride were added dropwise over about 2 hours to the aqueous slurry containing oxalic acid. Deionized water, 1,082 g, was added rapidly over about 3 minutes to the slurry at temperatures from about 9 to 24 degrees C. The slurry was warmed to a temperature of about 30 degrees C. for about 10 minutes to provide a clear solution. Concentrated ammonium hydroxide solution was added dropwise over about 2 hours at a temperature from about 25 to 30 degrees C. to provide a white slurry with a pH of about 9.0. The slurry was stirred for about 30 minutes while the pH was maintained at about 9.0 by the addition of small amounts of ammonium hydroxide. The total amount of concentrated ammonium hydroxide (about 29.5% NH3) consumed was approximately 1,336 g (about 22.7 moles). The white slurry was filtered and the wet cake washed with six 645 ml displacement washes of 2% ammonium hydroxide solution. The wet cake, which weighed about 1,327.6 g, was dried in a vacuum oven at about 120 degrees C. to provide about 550.5 g of amino titanium oxalate. The dry amino titanium oxalate was shown by ignition at 750 degrees C. for 3 hours to remove the volatiles to have a titanium dioxide content of about 43.27%. This represents a 99% by wt. yield.

Figure 3:
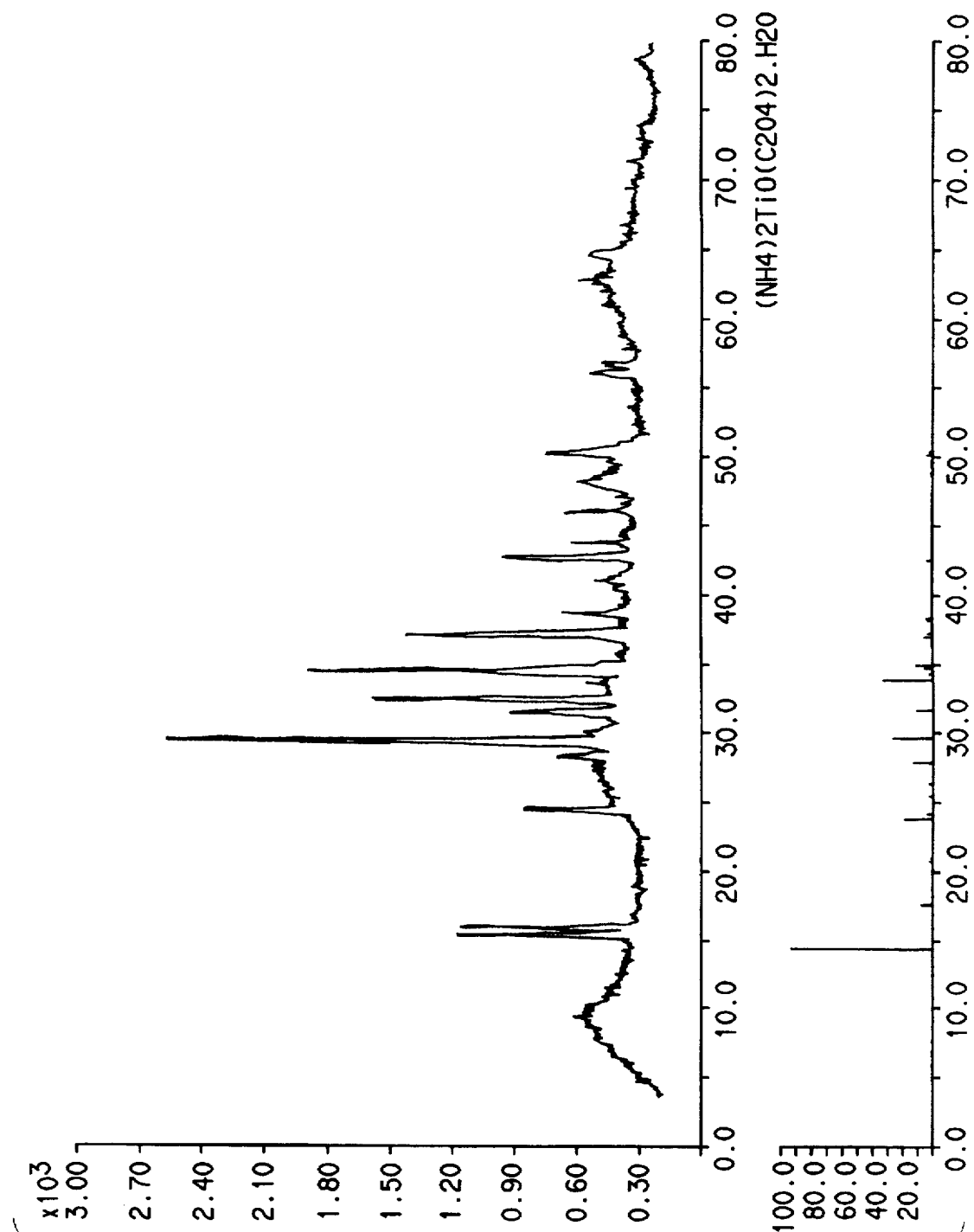
FIG. 3 is an X-ray diffraction pattern for the powder produced in accordance with Example 2A.

Referring now to FIG. 3, FIG. 3 is an X-ray diffraction pattern for the amino titanium oxalate produced in accordance with Example 2(A). An X-ray diffraction pattern for conventional ammonium titanium oxide oxalate hydrate was reported by A. Fester and M. Troemel, Institute fur Anorganische Chemie, Frankfurt, West Germany, ICDD Grant-In-Aid, 1989; hereby incorporated by reference. A comparison of FIG. 3 and the Troemel Pattern shows that the inventive amino titanium oxalate is distinct from conventional ammonium titanium oxide oxalate hydrate.

(B) Preparing ultrafine titanium dioxide by hydrothermally decomposing amino titanium oxalate:

Into a 1-gallon titanium autoclave equipped with a variable speed agitator, baffles, and a back pressure regulator, was charged amino titanium oxalate, (approximately 916.7 g, 43.27% $TiO_2$) which was prepared according to the procedure for Example 2, part (A), and about 2111 g of deionized water. After sealing the autoclave the agitator speed was set at 200 rpm and the pressure regulator was set at 400 psig. The contents of the autoclave were heated to about 200 to 205 degrees C. for over about 1 hour. The heating was continued at about 200 to 205 degrees C. for about 4 hours. The contents of the autoclave were then cooled to about 30 to 50 degrees C. over about 1 hour. The resultant white slurry from the autoclave was filtered and the wet cake washed with about 21 liters of deionized water. The wet cake, which weighed about 677.7 g, was found to contain about 381.8 g or a 96% by wt. yield, of ultrafine titanium dioxide.

Figure 4:
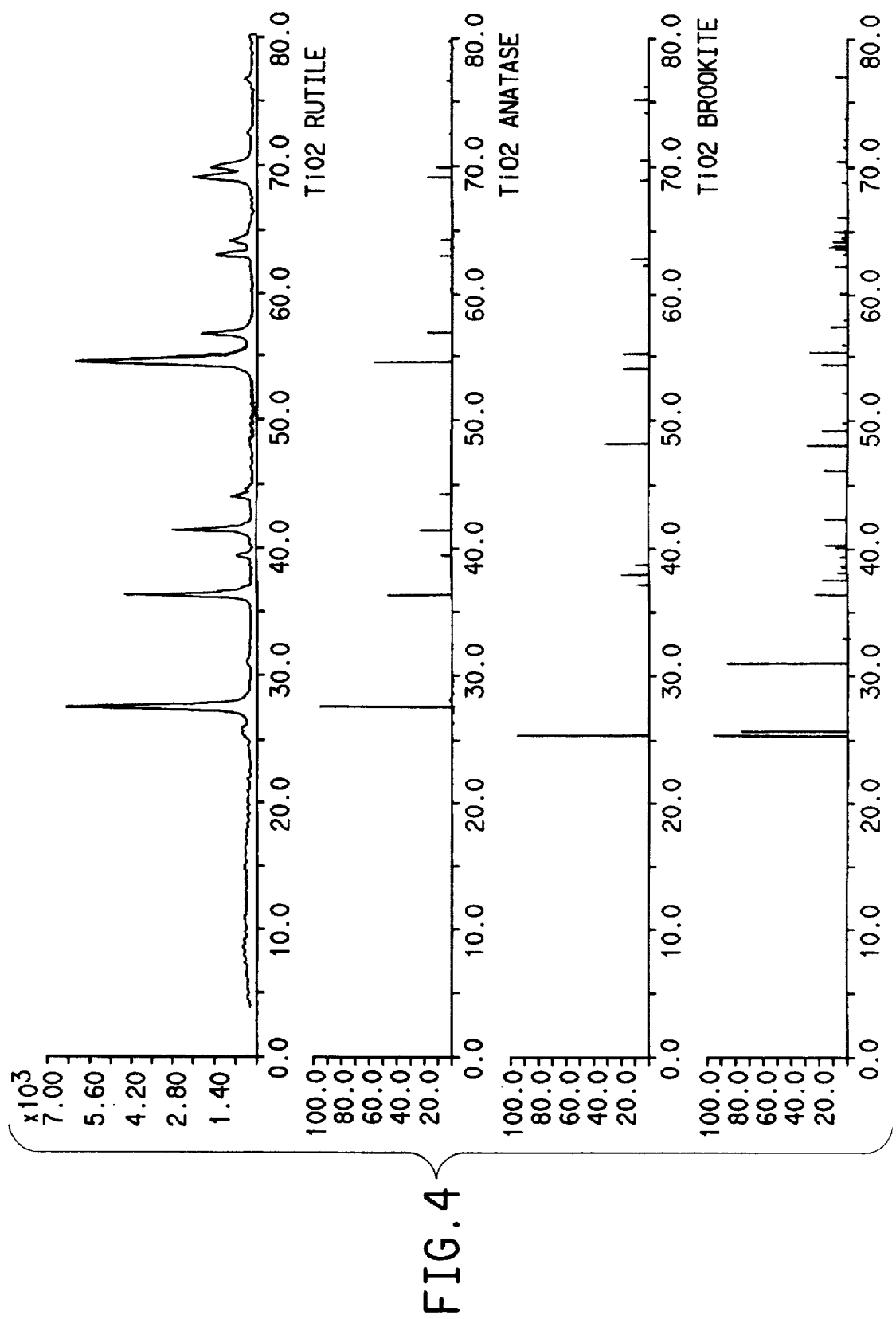
FIG. 4 is an X-ray diffraction pattern for the powder produced in accordance with Example 2B.

Referring now to FIG. 4, FIG. 4 is an X-ray diffraction pattern of the powder produced in accordance with Example 2(B). The X-ray pattern was generated by a Philips APD 1710 diffractometer in accordance with conventional techniques. The X-ray diffraction of the dry product indicated that it was about 97.5% by wt. rutile with the remainder being anatase and/or brookite. The primary rutile crystallite size was 45.6 nm. The powder was found to have an average agglomerate size (D50) of about 0.28 microns and a specific surface area of 40.1 m2/g.

Figure 5:
FIG. 5 is an TEM for the powder produced in accordance with Example 2B.

Referring now to FIG. 5, FIG. 5 is a TEM of the powder produced in accordance with Example 2(B). The Figure is at a magnification of 3×75 Kx wherein 1 cm=44 nm.

To determine the sun protection factor (SPF) and mean absorbance ratio (MAR), a master dispersion was prepared by mixing 30 g of ultrafine $TiO_2$ from Example 2, part (B), as described above, with about 15 g of a styrene-maleic anhydride dispersant, which is described in the aforementioned copending and commonly assigned U.S. patent application Ser. No. 08/548,988. (Attorney's Docket No. CH-2546), about 28% by weight in water, and 346 g of water. This mixture was milled in a Union Process 01 research attritor using 0.8 mm zirconium silicate beads at 500 rpm for 24 hours to provide a dispersion of finely divided particles of ultrafine powder. About 5 g of the master dispersion was mixed with about 18.2 g of Carboset 514H aqueous acrylic resin, available from B. F. Goodrich, to provide a dispersion containing 5% $TiO_2$ based on the dry weight of the $TiO_2$ and the resin. A drawdown of this dispersion was made onto a polypropylene sheet using a #8 rod. The SPF was determined by using the Optometirics SPF290 to be about 3.9. The MAR was determined by using the Optometrics SPF290 to be about 0.39.

To determine transparency of the $TiO_2$ powder from Example 2, part (B), as described above, in formulations, the following procedure was used to prepare a film containing the powder.

Approximately 1 g of the aforementioned master dispersion was mixed with about 4.4 g of Eastman AQ38, an aqueous polyester resin, 30% by weight in water (available from Eastman Chemicals), to provide a dispersion containing 5.4% $TiO_2$ based on the dry weight of the $TiO_2$ and the resin. A drawdown of this dispersion was made onto a polyester sheet using a #8 rod. The haze value of the film was 20.5% and the transmittance was 88.8%.

EXAMPLE 3

(A) Preparing amino zinc oxalate:

Deionized water (approximately 800 g) and about 254.8 g (2.0 moles) of oxalic acid dihydrate were charged to a 3-liter flask that was maintained under a nitrogen atmosphere. The slurry was warmed to a temperature of about 35 degrees C. to dissolve substantially all of the oxalic acid. The slurry was cooled to about 25–30 degrees C., and then about 137.2 g (1.0 mole) of zinc chloride was added over about a period of about 5 minutes. The resultant white slurry was agitated at about 25 degrees C. for 30 minutes. Concentrated ammonium hydroxide was added dropwise over about 1 hour at about 25–30 degrees C. to give a white slurry with a pH of about 9. The slurry was allowed to agitate for about 30 minutes while the pH was maintained at about 9 by the addition of small amounts of ammonium hydroxide. The total amount of ammonium hydroxide consumed was approximately 317.7 g (5.41 moles). The resultant white slurry was filtered and the filter cake washed with four 600 ml displacement washes of 2% ammonium hydroxide. The wet cake was dried at a temperature of about 120 degrees C. in a vacuum oven and produced about 184.1 g of product. Based on ignition (at 750 degrees C.) this dried cake product was found to contain about 38.39% ZnO.

(B) Preparing ultrafine zinc oxide by the hydrothermally decomposing amino zinc oxalate:

Amino zinc oxalate, about 80 g that was obtained from Example 3, part (A), and about 48.35 g (0.7548 mole potassium hydroxide—87.6% KOH in 192 g of deionized water), were charged to a 400 ml tantalum shaker bomb. The bomb was sealed and the contents heated to a temperature of about 200–205 degrees C. for 3 hours while gently shaking. The bomb was cooled to about 25 degrees C., the resulting white slurry filtered, and the filter cake (46.4 g) was dried in a vacuum oven at a temperature of about 120 degrees C. to give approximately 28.8 g of ultrafine zinc oxide.

The white zinc oxide powder was examined by X-ray diffraction on a Philips APD 1710 diffractometer in accordance with conventional techniques. The white powder was shown by x-ray diffraction to be zinc oxide with a primary crystallite size of about 54 nm. The average agglomerate size (D50) was 0.6 microns. The specific surface area of this ultrafine zinc oxide was about 45.4 m2/g.

SPF and MAR were determined by using the techniques described above in Example 2. The ultrafine zinc oxide appeared to dissolve in the resin and turned yellow. SPF was determined to be 1.0 and the MAR was 1.9.

Haze and transmittance were also determined by using the techniques described above in Example 2. Haze was determined to be about 6.1% at a transmittance value of 90.3%.

EXAMPLE 4

(A) Preparing tin/antimony amino oxalate:

Deionized water (approximately 940 g) and 170.9 g (about 1.356 moles) of oxalic acid dihydrate were charged to 3-liter flask that was maintained under a nitrogen atmosphere. The resultant slurry was warmed to a temperature of about 30 degrees C. to obtain a clear solution. A solution comprised of about 57.9 g (0.0746 mole) of antimony trichloride solution (0.23 g Sb/ml) and 309.7 g (0.6032 mole) stannic chloride solution (50% $SnCl_4$) was added rapidly to the clear oxalic acid solution over about 1 minute at about 25–30 degrees C. The solution was agitated for about 5 minutes during which a white precipitate formed. Concentrated ammonium hydroxide was added dropwise over about 50 minutes at about 25–30 degrees C. to give a white slurry with pH of about 6.5. The slurry was agitated for 1 hour while the pH was maintained at about 6.5 by adding small increments of ammonium hydroxide. The total amount of concentrated ammonium hydroxide consumed was about 288.7 g (5.08 moles). The white slurry was filtered, and the filter cake washed with five 400 ml displacement washes of 2.5% ammonium oxalate solution that produced about 391 g of product. About 380 g of the wet cake was dried in a vacuum oven at a temperature of about 85–90 degrees C. thereby producing about 94 g of a yellow-tan powder.

(B) Preparing ultrafine antimony doped tin oxide by the hydrothermally decomposing tin/antimony amino oxalate.

The tin/antimony complex from Example 4, part (A) (approximately 40 g) and 250 g of deionized water were charged to a 400 ml tantalum shaker bomb. The bomb was sealed and the contents heated to a temperature of about 200–205 degrees C. for about 3 hours while gently shaking. The bomb was cooled to about 25 degrees C., the resulting bluish gray slurry was filtered and the filter cake washed with about 3000 ml of deionized water. The filter cake (16 g) was dried at a temperature of about 110° C. in a vacuum oven to produce about 11.5 g of a gray powder. The powder was examined by conventional X-ray diffraction techniques and was shown to have an X-ray diffraction pattern similar to tin oxide with a primary crystallite size of about 5 nm.

A 4 gram sample of the dried powder was calcined in an air atmosphere at a temperature of about 500 degrees C. for 1 hour. The resulting gray powder was shown to have an X-ray diffraction pattern similar to tin oxide with a primary crystallite size of about 5 nm. The specific surface area of this powder was measured by conventional techniques to be about 101.7 m2/g. The calcined powder was shown to have a conductivity, which was also determined by using conventional techniques, of about 0.125 ohm-cm(−1).

EXAMPLE 5

(A) Preparing amino aluminum oxalate:

Deionized water (approximately 1,000 g) and oxalic acid dihydrate 254.7 g (2.0 moles) were charged into a 3-liter flask that was maintained under a nitrogen atmosphere. The slurry was cooled to about 5–10 degrees C. Anhydrous aluminum chloride about 133.4 g (1.0 mole) was added in about 10 g portions at about 5–10 degrees C. over a period of about 2 hours. The solution was warmed to a temperature of about 25–30 degrees C. Concentrated ammonium hydroxide solution was added dropwise over about 1.5 hours at a temperature of about 25–30 degrees C. to produce a grayish white slurry with a pH of about 10. The slurry was agitated at a temperature of about 25–30 degrees C. for 30 minutes.

The total amount of concentrated ammonium hydroxide consumed was approximately 712.1 g (12.1 moles). The resultant white slurry was filtered and the wet cake washed with six 400 ml displacement washes of 6% ammonium hydroxide solution. The process produced about 547 g of wet product.

(B) Preparing ultrafine boehmite (aluminum oxide hydroxide) by the hydrothermally decomposing amino aluminum oxalate:

An approximately 214.4 g sample of the wet aluminum oxlate from Example 5 part (A), was fluidized with about 105.6 g of deionized water. The resultant slurry was charged into a 400 ml tantalum shaker bomb. The bomb was sealed and the contents heated to a temperature of about 200–205 degrees C. for 3 hours while gently shaking. The bomb was cooled to about 25 degrees C., the resulting thick paste was filtered and the filter cake washed with about 2100 ml of deionized water. The wet cake (74.5 g) was dried in a vacuum oven at a temperature of about 120 degrees C. to produce about 22.3 g of ultrafine boehmite.

The powder was examined by using X-ray diffraction analysis. The X-ray diffraction determined the powder to be boehmite with a primary crystallite size of about 14 nm. The specific surface area of the powder was about 116.7 m2/g.

EXAMPLE 6

(A) Preparing titanium/tin amino oxalate:

Deionized water (approximately 500 g) and about 133.7 g (1.042 mole) of oxalic acid dihydrate were charged into a 3-liter flask that was maintained under a nitrogen atmosphere. The slurry was warmed to a temperature of about 42 degrees C. to dissolve substantially all of the oxalic acid. A solution comprised of about 11.1 g (0.0212 mole) stannic chloride solution (50% $SnCl_4$) and 383.2 g (1.0 mole) of titanium oxychloride solution (12.5% Ti) was added rapidly to the oxalic acid solution that was at a temperature of from about 42–59 degrees C. The resulting solution was cooled to about 25 degrees C. Concentrated ammonium hydroxide solution was added dropwise over about 35 minutes at about 25–30 degrees C. to produce a white slurry with a pH of about 9. The white slurry was agitated for about 40 minutes while the pH was maintained at about 9 by the addition of small amounts of ammonium hydroxide. The total amount of concentrated ammonium hydroxide consumed was about 405.5 g (7.02 moles). The white slurry was filtered, and the filter cake washed with six 215 ml displacement washes of 2% ammonium hydroxide. The filter cake was dried at a temperature of about 120 degrees C. in a vacuum oven to produce 175 g of the amino product.

(B) Preparing ultrafine tin oxide doped titanium dioxide by the hydrothermally decomposing titanium/tin amino oxalate:

The titanium/tin amino oxalate, 80 g. from Example 6, part (A), as described above, and 240 g of deionized water were charged to a 400 ml tantalum shaker bomb. The bomb was sealed and the contents heated at about 200–205 degrees C. for a period of about 3 hours. The bomb was cooled to about 25 degrees C., the resulting white slurry was filtered and the filter cake washed with about 3,700 ml of deionized water. The wet cake was dried at a temperature of about 120 degrees C. in a vacuum oven to produce about 37 g of ultrafine tin doped titanium dioxide. The product was shown by inductively couple plasma (ICP) analysis on a Perkin Elmer Plasma-II to have a $SnO_2$ content of about 4%.

Figure 6:
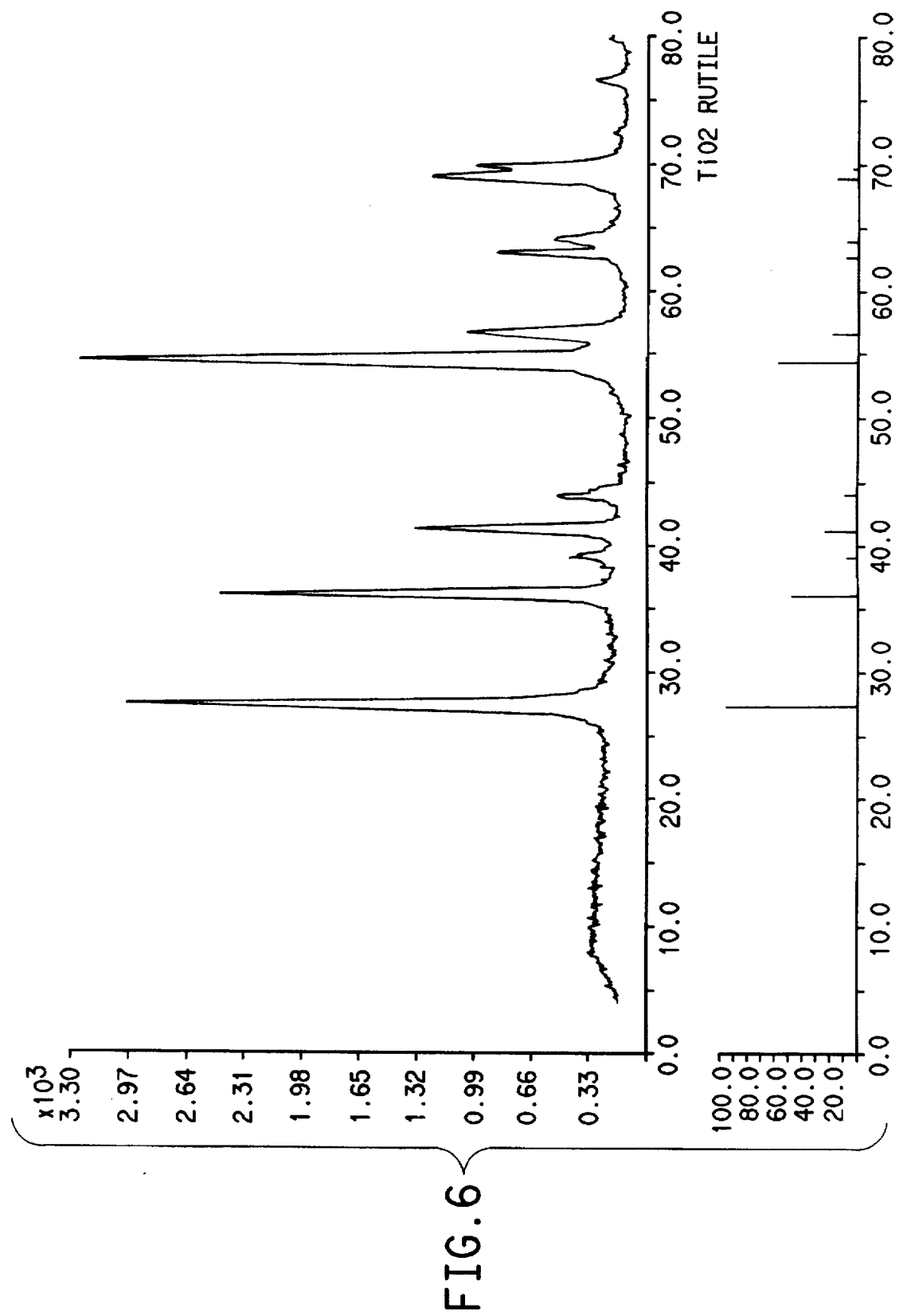
FIG. 6 is an X-ray diffraction pattern for the powder produced in accordance with Example 6B.

Referring now to FIG. 6, FIG. 6 is an X-ray diffraction pattern, which was produced in accordance with conventional techniques, of the dried powder. The white powder was shown by X-ray diffraction to be mostly rutile with a primary crystallite size of about 15 nm. The specific surface area of this ultrafine powder was about 81.9 m2/g.

Figure 7:
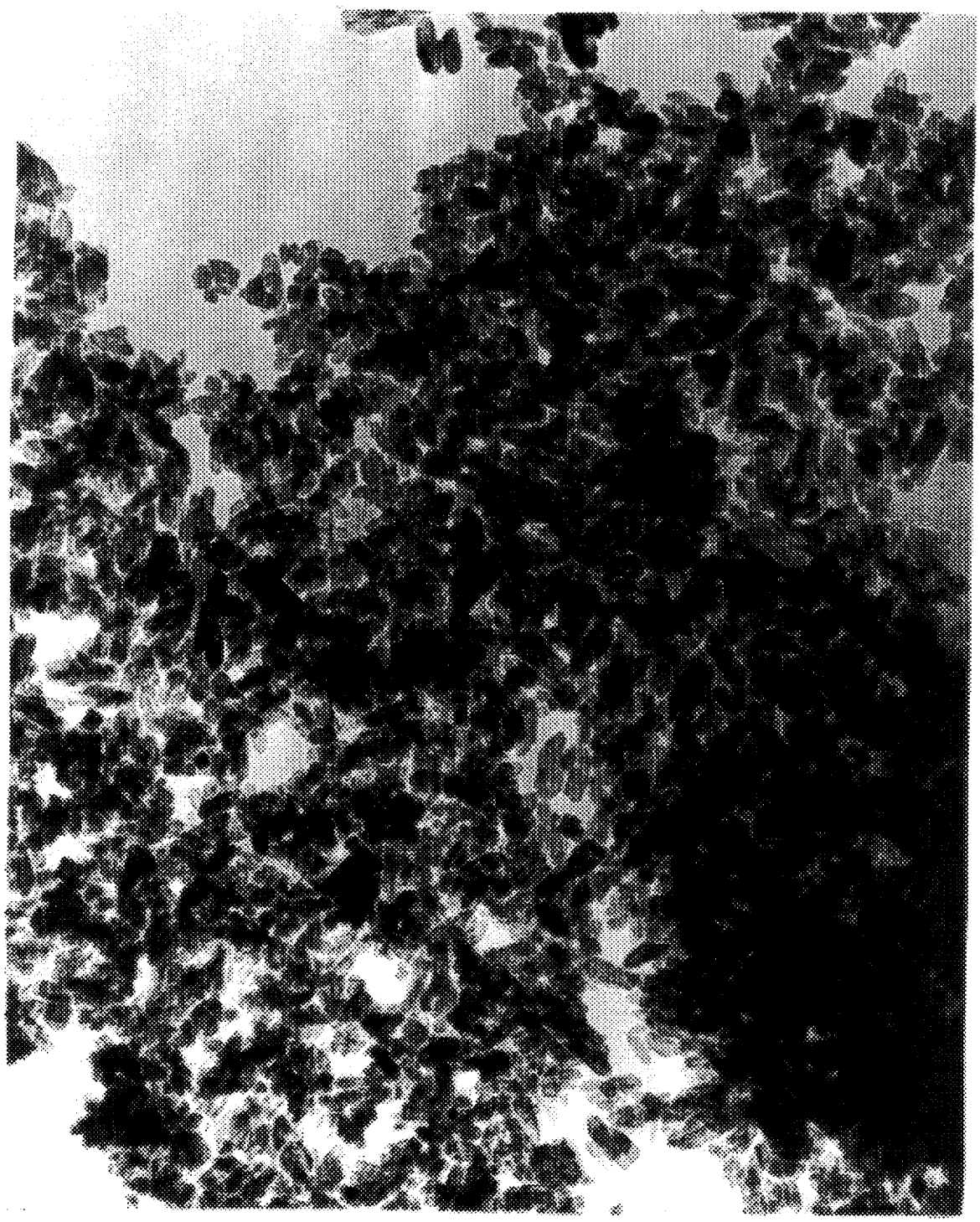
FIG. 7 is an TEM for the powder produced in accordance with Example 6B.

Referring now to FIG. 7, FIG. 7 is a transmission electron microscopy (TEM) photograph of the powder. FIG. 7 shows that the powder consisted of small aggregates of plates with the average aggregate size at about 57 nm.

SPF and MAR were determined in accordance with the procedure described above in Example 2. SPF was determined to be about 8.4 and the MAR was about 0.26.

Haze and transmittance were determined in accordance with the procedure described about in Example 2. Haze was determined to be about 4.3% at a transmittance value of about 88.9%.

EXAMPLE 7

(A) Preparing titanium/aluminum amino oxalate:

Deionized water (approximately 500 g) and about 127.3 g (1 mole) of oxalic acid dihydrate were charged into a 3-liter flask that was maintained under a nitrogen atmosphere. The slurry was warmed to a temperature of about 40 degrees C. to dissolve substantially all the of the oxalic acid.

A solution was prepared by dissolving about 4.18 g of anhydrous aluminum chloride in approximately 383.2 g (1 mole) titanium oxychloride solution (about 12.5% Ti). This solution was added rapidly to the oxalic acid solution at a temperature of from about 42–62 degrees C. The resulting light yellow solution was cooled to about 25–30 degrees C. Concentrated ammonium hydroxide solution was added dropwise over about 45 minutes at about 25–30 degrees C. to produce a white slurry with a pH of about 10. The slurry was agitated for about 3 hours at about pH 10. The total amount of concentrated ammonium hydroxide consumed was about 640.2 g (10.9 moles). The white slurry was filtered and the filter cake washed with six 215 ml displacement washes of 2% ammonium hydroxide solution. The wet cake was dried at a temperature of about 120 degrees C. in a vacuum oven to produce 169 g of dried powder.

(B) Preparing ultrafine aluminum oxide doped titanium dioxide by the hydrothermally decomposing titanium/aluminum amino oxalate:

The aluminum doped titanium product from Example 7, part (A), approximately 80 g and about 240 g of deionized water were charged into a 400 ml tantalum shaker bomb. The bomb was sealed and the contents heated at a temperature of about 200–205 degrees C. for about 3 hours while gently shaking. The bomb was cooled to about 25 degrees C., the resulting white slurry filtered and the filter cake washed with about 5,000 ml of deionized water. The wet cake was dried to produce about 37.1 g of ultrafine aluminum doped titanium dioxide.

Figure 8:
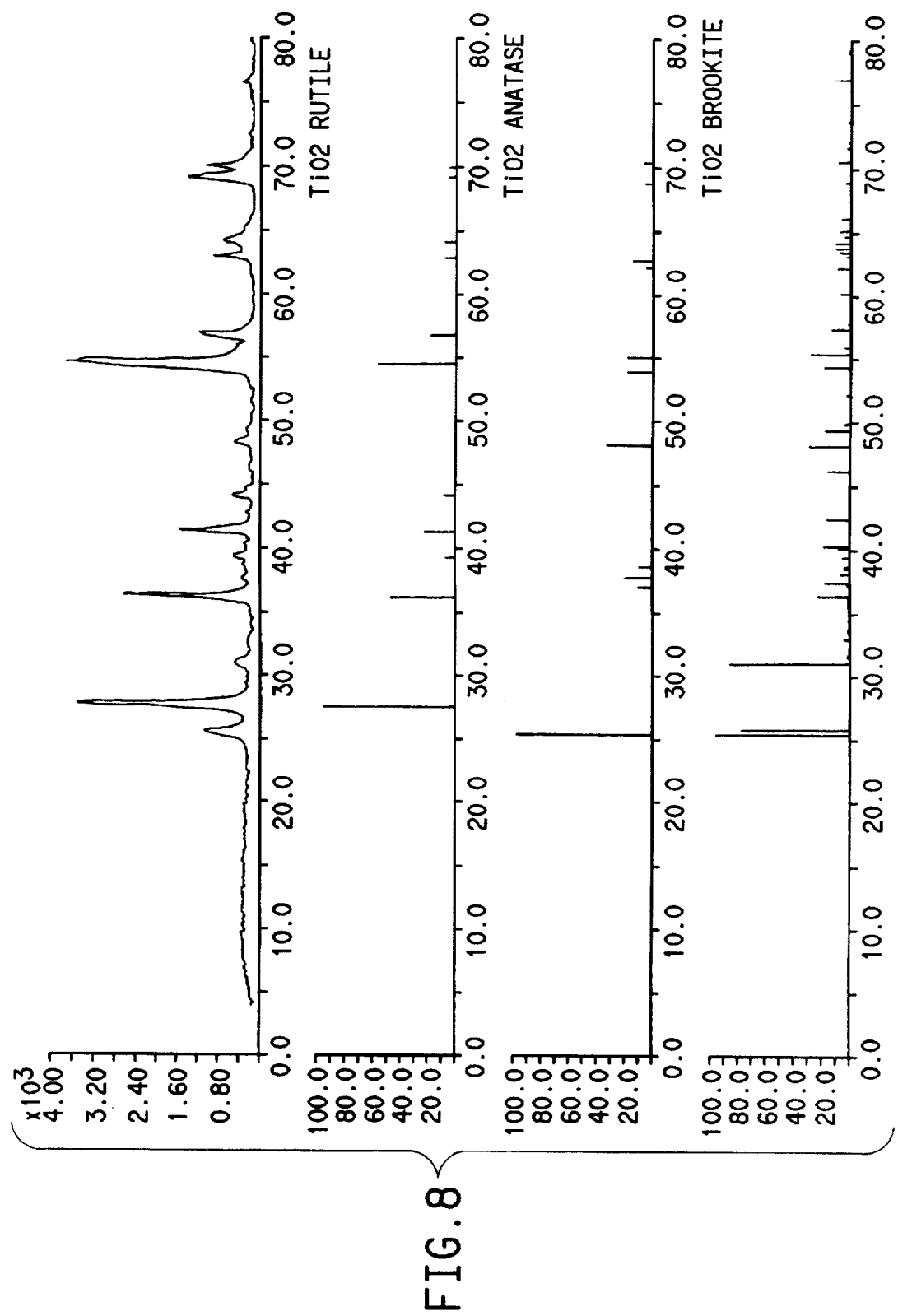
FIG. 8 is an X-ray diffraction pattern for the powder produced in accordance with Example 7B.

The product was shown by using conventional ICP analysis techniques to have a $Al_2O_3$ content of about 0.2%. Referring now to FIG. 8, FIG. 8 is an X-ray diffraction pattern of the aforementioned dried product that was produced in accordance with conventional techniques. The powder was shown by X-ray diffraction to be about 88% rutile with a minor phase of anatase and/or brookite. The rutile crystallite size was about 35 nm. The average agglomerate size was 0.24 microns. The powder had a specific surface area of about 59 m2/g.

Figure 9:
FIG. 9 is an TEM for the powder produced in accordance with Example 7B.

Referring now to FIG. 9, FIG. 9 is a transmission electron microscopy (TEM) of the aforementioned dried powder. The TEM of the powder revealed that the powder consisted of plates (about 257×74 nm) and fines about of 11 nm.

SPF and MAR were determined in accordance with the techniques described in Example 2. SPF was determined to be about 4.8 and the MAR was about 0.33.

Haze and transmittance were also determined in accordance with the techniques described in Example 2. Haze was determined to be about 11.0% at a transmittance value of about 88.8%.

EXAMPLE 8

(A) Preparing titanium/tin amino oxalate:

Deionized water, approximately 500 g, and oxalic acid dihydrate, about 127.3 g (1.0 mole) were charged into a 3-liter flask that was maintained under a nitrogen atmosphere. The resultant slurry was warmed to a temperature of about 39 degrees C. to dissolve all of the oxalic acid.

A solution comprised of about 5.57 g (0.0106 mole) stannic chloride solution (50% $SnCl_4$) and 383.2 g (1.0 mole) of titanium oxychloride solution (about 12.5% Ti) was added rapidly to the oxalic acid solution at a temperature from about 39 degrees C. to about 55 degrees C. The resulting solution was cooled to about 23 degrees C. Concentrated ammonium hydroxide (about 29.5% $NH_3$) was added dropwise over about 45 minutes at about 25–30 degrees C. to produce a white slurry with a pH of about 9. The slurry was agitated for about 30 minutes while the pH was maintained at about 9 by the addition of small increments of concentrated ammonium hydroxide. The total amount of concentrated ammonium hydroxide consumed was about 399.4 g (6.92 moles). The white slurry was filtered and the filter cake washed with six 215 ml displacement washes of 2% ammonium hydroxide solution. The filter cake was dried at a temperature of about 120 degrees in a vacuum oven to produce about 166.8 g of product.

(B) Preparing ultrafine tin oxide doped titanium dioxide by the hydrothermally decomposing titanium/tin amino oxalate:

The tin doped titanium product from Example 8, part (A), about 80 g, and 240 g of deionized water were charged into a 400 ml tantalum shaker bomb. The bomb was sealed and the contents heated to a temperature of about 200–205 degrees C. for about 3 hours. The bomb was cooled to about 25 degrees C., the resulting white slurry was filtered, and the filter cake was washed with about 5,400 ml of deionized water. The wet cake was dried at a temperature of about 120 degrees C. in a vacuum oven to produce about 36.9 g of tin doped ultrafine titanium dioxide. The product was shown by using conventional ICP analysis techniques to have a $SnO_2$ content of about 1.81%.

Figure 10:
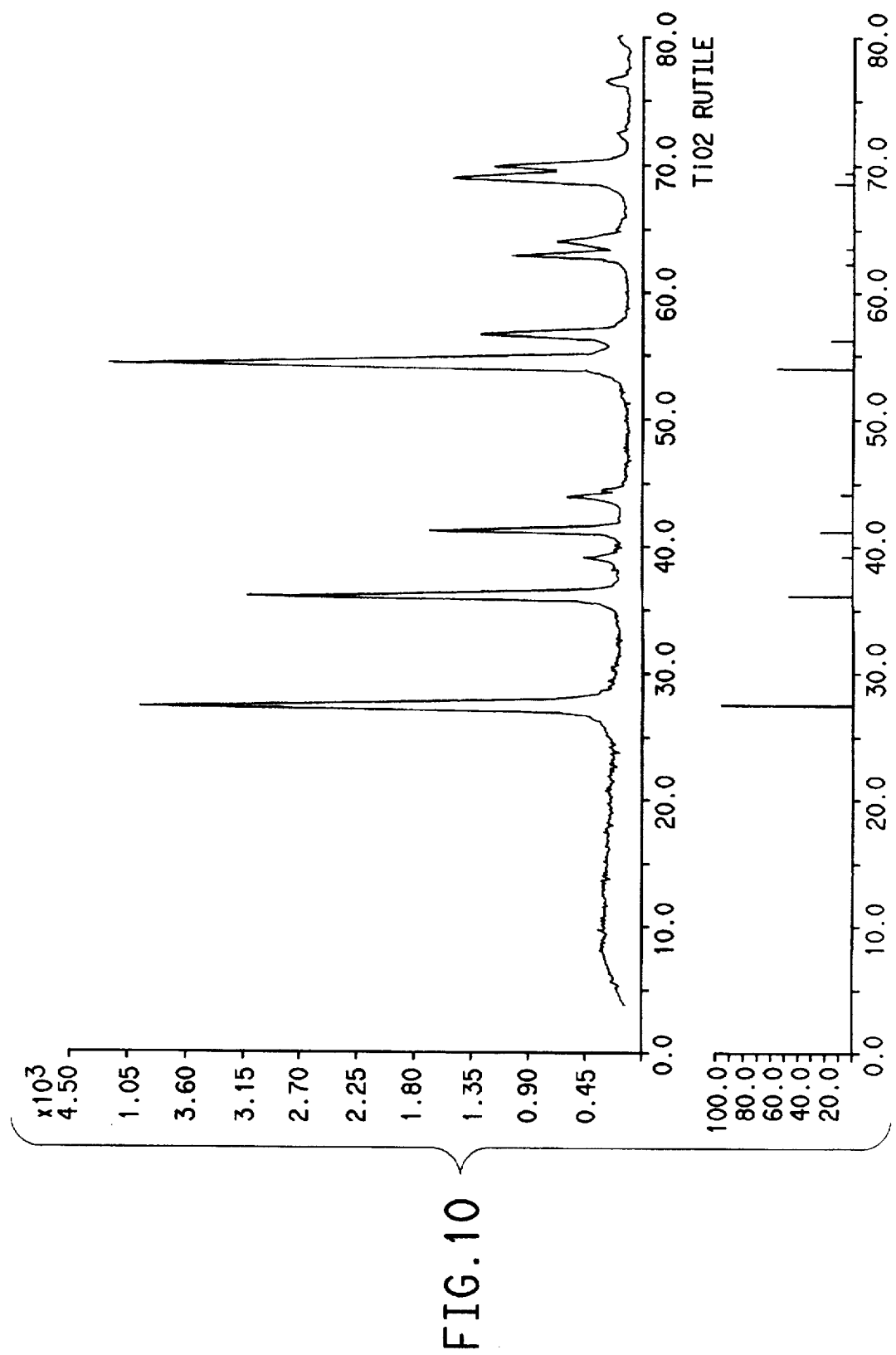
FIG. 10 is an X-ray diffraction pattern for the powder produced in accordance with Example 8B.

Referring now to FIG. 10. FIG. 10 is an X-ray diffraction pattern of the dried product that was obtained by using conventional techniques. The X-ray diffraction of the white powder indicated that the powder was in the rutile form with a primary crystallite size of about 22 nm. The specific surface area of this ultrafine powder was about 57.8 m2/g.

Figure 11:
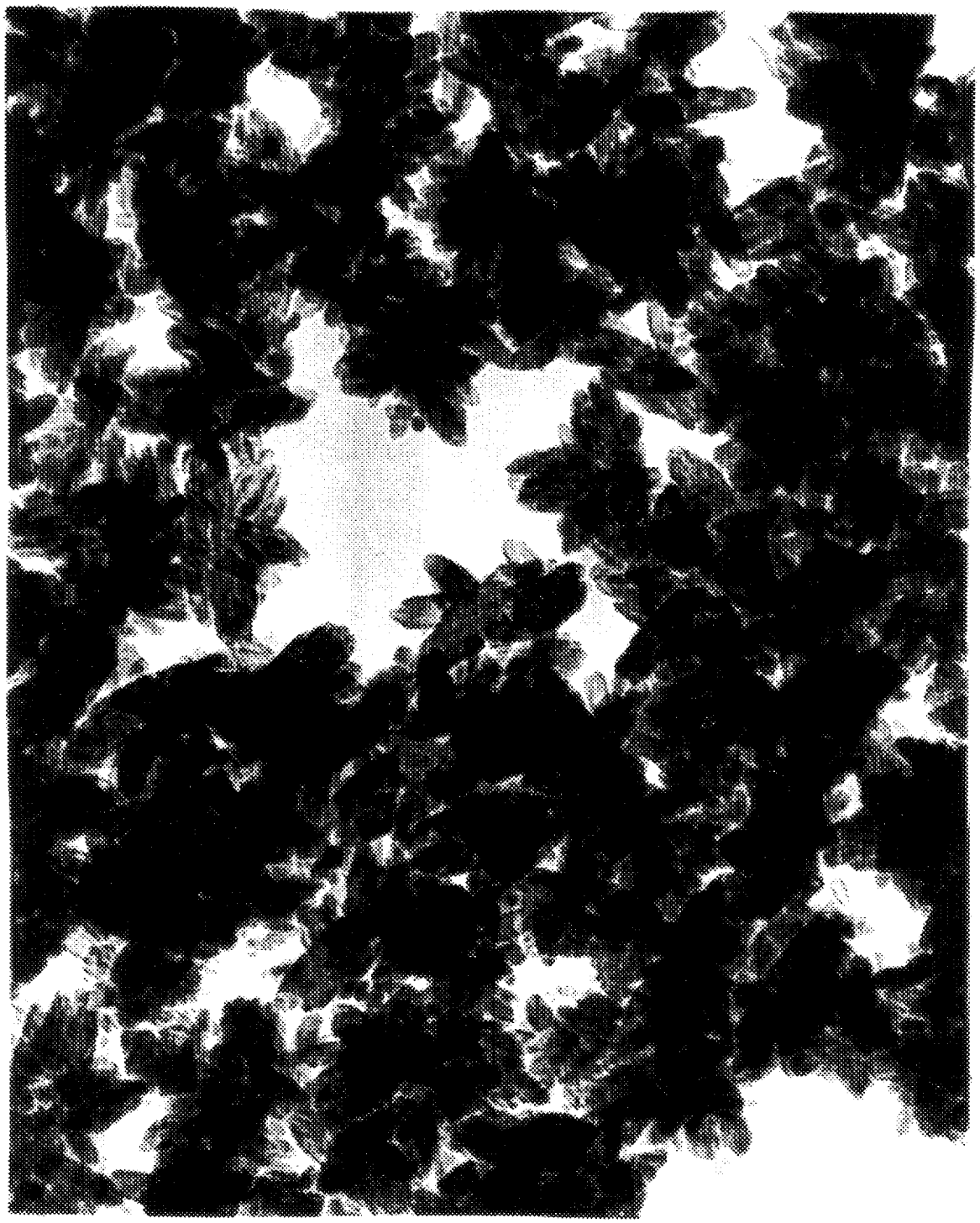
FIG. 11 is an TEM for the powder produced in accordance with Example 8B.

Referring now to FIG. 11. FIG. 11 is a transmission electron microscopy (TEM) of the powder. The TEM indicates that the powder consisted of aggregates of ellipsoidal plates, with the aggregate size being about 157 nm.

SPF and MAR were determined in accordance with the procedures described in Example 2. SPF was determined to be about 4.4 and the MAR was about 0.40.

Haze and transmittance were determined in accordance with the procedures described in Example 2. Haze was determined to be about 27.2% at a transmittance value of about 90.1%.

The following is claimed:

1. A process for making an inorganic powder comprising:

preparing an aqueous solution comprising oxalic acid, adding a hydrolyzable metal compound to the aqueous solution of oxalic acid at a molar ratio of oxalic acid to metal compound of from about 0.9:1 to about 1.1:1, optionally, adding deionized water, adding ammonia or ammonium hydroxide solution, adjusting the pH of the solution to about 8–10 thereby forming a slurry containing a solid comprising an amino metal oxalate having the structure

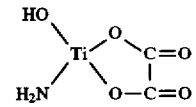

recovering said oxalate via filtration, and reacting said oxalate with water at a temperature of about 200° C. to 250° C. under pressure to yield an inorganic metal oxide powder.

2. The process of claim 1 wherein the amino metal oxalate contains a metal selected from the group consisting of zinc, tin, antimony mixed with tin, iron, zirconium, aluminum, chromium, yttrium and europium.

3. The process of claim 1 wherein said powder comprises:

at least one oxide of metals selected from the group of titanium, zirconium, silicon, aluminum, yttrium, europium, tin, antimony, iron, zinc, wherein said powder has an average crystallite size of about 1 to 100 nm.

4. The process of claim 1 wherein said process is performed in a non-oxidizing atmosphere.

5. The process of claim 1 wherein said process is performed in the presence of at least one dopant metal selected from the group consisting of tin, titanium, aluminum, antimony, zirconium, zinc, cerium, germanium, manganese, vanadium, ruthenium, iridium, osmium, tungsten, molybdenum, niobium, cobalt, lead, silicon, indium, tantalum, yttrium, europium, iron, copper and nickel; wherein said metals and said dopant metals are chemically distinct.

* * * * *